United States Patent [19]

Trimble

[11] Patent Number: 5,437,284
[45] Date of Patent: Aug. 1, 1995

[54] SYSTEM AND METHOD FOR IN VIVO CALIBRATION OF A SENSOR

[75] Inventor: Brett A. Trimble, Del Mar, Calif.

[73] Assignee: Camino Laboratories, Inc., San Diego, Calif.

[21] Appl. No.: 175,871

[22] Filed: Dec. 30, 1993

[51] Int. Cl.⁶ ............................................. A61B 5/00
[52] U.S. Cl. ..................................... 128/673; 73/4 R
[58] Field of Search .................. 73/4 R, 1 B; 128/673

[56] References Cited

U.S. PATENT DOCUMENTS

| | | | |
|---|---|---|---|
| 4,446,715 | 5/1984 | Bailey | 73/1 R |
| 4,712,566 | 12/1987 | Hök | 73/4 R |
| 4,815,513 | 3/1989 | Beard | 73/4 R |
| 5,065,010 | 11/1991 | Knute | 250/277.21 |
| 5,203,340 | 4/1993 | Gustafson et al. | 73/4 R |
| 5,247,171 | 9/1993 | Wlodarczyk et al. | 250/227.21 |

FOREIGN PATENT DOCUMENTS

0475686A1  3/1992  European Pat. Off.
91/05575  5/1991  WIPO.

OTHER PUBLICATIONS

Sensors May 1992, pp. 31–33 "A Disposable BP Transducer for in Vivo Pressure Measurements".

Primary Examiner—Richard E. Chilcot, Jr.
Assistant Examiner—Max H. Noori
Attorney, Agent, or Firm—Fulwider, Patton, Lee & Utecht

[57] ABSTRACT

Calibration apparatus and method for calibrating a movable pressure sensor include the use of a stop device to establish a reference position outside the sensing movement range of a first sensor. While in vitro, a reference pressure is established by applying pressure to the sensor to move it against the stop surface with a controllable pressure source. This reference pressure is stored. During use when the sensor is in an unknown position, such as when in vivo, the controllable pressure source applies pressure to move the sensor against the stop surface and the pressure required to do so is measured. The measured pressure is compared to the reference pressure to determine the unknown pressure and the system is then recalibrated. An optical system may be used as a second sensor to determine the position of the first sensor. Inner and outer housings in which the first sensor and stop surface are mounted are moved in relation to each other and the optical sensor during assembly of the calibration system to accurately and independently calibrate the first and optical sensors.

22 Claims, 7 Drawing Sheets

SYSTEM AND METHOD FOR IN VIVO CALIBRATION OF A SENSOR

The invention is generally related to sensors and more particularly, is related to calibrating sensing systems while they are in use.

Monitoring intracranial pressure can be critical to the treatment of a head injury. The resultant swelling of intracranial tissues can cause additional injury and even death to the patient unless the excess pressure is relieved. An intracranial pressure sensor can assist the attending physician in management of the head injury case by providing information concerning the pressure affecting the brain. Through continuous pressure monitoring, the physician is better informed and can take action should the pressure reach an unacceptable level or indicate other conditions of the brain.

In many cases, the pressure sensor must be left in place for an extended period; for example, five days. During this time, the sensor system may drift out of calibration and its readings become less accurate. One solution to correct calibration drift is to remove the pressure sensor and re-calibrate the sensor system while the sensor is removed. However, removing the pressure sensor for re-calibration is not desirable due to the increased possibility of infection of the patient and additional trauma. At the same time though, it is desirable to undertake re-calibration of the pressure sensor during these extended periods of use so that any calibration drift of the sensor is detected and eliminated.

In general, two broad classes of pressure sensing catheters are used for intracranial pressure monitoring. The conventional method employs a hollow tube that is introduced through the cranium into a fluid space in the brain and is in fluid communication with a strain gauge external to the patient. This fluid filled system has the advantage of the possibility of re-calibration when in use because the transducer is located outside the patient and can therefore be isolated from patient pressure; for example, through the use of a valve. However, this system has the disadvantages of increased risk of infection to the patient and sensitivity to patient movement.

A more recent approach employs a miniaturized transducer placed at the distal end of a catheter. This transducer-equipped distal end of the catheter is inserted through the cranium and into the brain to monitor pressures. While this approach has the advantages of a lessened risk of patient infection and relative insensitivity to patient movement, the ability to perform in vivo re-calibration has not been available in a manner that at the same time provides cost effectiveness and increased accuracy. A transducer tipped catheter that could be re-calibrated in vivo would provide the physician with the added assurance of correct pressure data over long periods of time.

Many pressure sensors employ a diaphragm as a primary transducer. This diaphragm moves in response to changes in patient pressure, referenced to atmospheric. Moving the diaphragm against a physical stop, positioned at the diaphragm zero pressure position, by applying calibration pressure to the side of the diaphragm that normally is exposed to atmospheric pressure has been proposed as a means of in vivo re-calibration. In this arrangement a halt in the change in output of the secondary transducer that is sensitive to diaphragm displacement indicates that the stop has been reached by the diaphragm, and therefore the differential zero pressure position, has been reached. With the diaphragm in this position the display is then re-zeroed as necessary. A technique of this type is disclosed in international PCT patent application WO 91/05575.

Manufacturing a pressure sensor assembly such that a pressure sensor diaphragm is always located against a stop at atmospheric (zero differential) pressure presents some manufacturing challenges related to the positioning of components. If the diaphragm does not rest against the stop at atmospheric pressure, forcing it against the stop during the in vivo re-calibration will result in inaccuracy. The small size required for medical applications (for example 0.050 inches (1.27 mm) diameter), the small diaphragm displacements involved (for example 0.001 inches (0.025 mm) or less for 250 mm Hg differential pressure) and the need to position the diaphragm in a sensitive region of the transfer function of the secondary transducer all contribute to the difficulty in locating a stop at the diaphragm zero position. This difficulty results in increased manufacturing complexity and cost. In the case where such pressure sensors are meant to be disposable, an increased manufacturing expense is undesirable.

Hence, those concerned with the use of sensors have recognized the need for an improved, relatively simple, economical, durable, and reliable recalibrating system that permits re-calibration of the sensor system while in vivo. Those concerned have also recognized the desirability of providing such a re-calibrating system that is relatively inexpensive to manufacture yet provides improved accuracy in pressure sensors. The present invention fulfills these needs and others.

SUMMARY OF THE INVENTION

Briefly and in general terms, the present invention in one aspect is directed to a calibration system and method that permit accurate in vivo calibration of a sensor system. In a more detailed aspect of the invention, a calibration system is provided for calibrating a sensor system having a first sensor that moves within a range when sensing a physiological parameter. The sensor system also has a processing system that monitors the position of the first sensor and provides an output signal representative of the physiological parameter based on the monitored position of the first sensor. The calibration system comprises a stop device located so as to restrict the first sensor to a known position outside the sensing movement range when the sensor is engaged with the stop device. Additionally, a controllable force generator is provided that selectively applies force to the first sensor to move it into contact with the stop device. A force gauge measures the force applied by the force generator and provides a measured force signal representative of the force applied by the force generator to move the first sensor into contact with the stop device. A memory has stored therein a reference force required to move the first sensor from a selected position, at which the first sensor was subjected to a first force, to the stop device. The processing system controls the force generator to apply force to the first sensor to move it from an unknown position resulting from an unknown force acting upon the first sensor to the stop device, receives the measured force signal from the force gauge, retrieves the reference force, and determines the value of the unknown force based on comparing the reference force to the measured force.

In another aspect, the first sensor movement range comprises a maximum position at which the first sensor would be located should the physiological parameter reach a maximum predetermined level and the stop device is located outside the first sensor movement range and beyond the maximum position. In a further aspect, the force generator selectively applies a reduced pressure against the first sensor to urge it into contact with the stop device.

In yet a further aspect, the first sensor is located in an enclosed area that surrounds one end of the first sensor and a vent tube is coupled to the enclosed area. The reduced pressure is applied to the first sensor through the vent tube. In further aspects in accordance with the inventions, the first sensor is mounted in an outer housing, the outer housing having a first opening for transferring the physiological parameter to the first sensor, the outer housing having a second opening. An inner housing is mounted in the second opening of the first housing at a selected position and provides the stop device and an access port through which the force may be applied by the force generator to the first sensor, wherein the inner housing and associated stop device are mounted opposite the first opening and beyond the maximum position. Additionally, in another aspect, the processing system additionally controls the force generator to apply force to move the first sensing element into contact with the stop device.

In yet a further aspect, the calibration system is further for calibrating a sensor system that additionally comprises a second sensor that determines the position of the first sensor in sensing the physiological parameter, the second sensor being responsive to the distance of the first sensor from the second sensor. The calibration system further comprises a first housing within which the first sensor is mounted and a second housing having the stop device. The first housing and second housing are movable in relation to each other along the direction of movement of the first sensor to permit the sensing movement range of the first sensor and to locate the stop surface outside that movement range. The second housing is movable in relation to the second sensor so that the first sensor may be located at a desired distance from the second sensor.

In a calibration method in accordance with an aspect of the invention, a sensor system having a first sensor that moves within a range when sensing a physiological parameter may be calibrated. The sensor system also having a processing system that monitors the position of the first sensor and provides an output signal representative of the physiological parameter based on the monitored position of the first sensor. The method of calibrating in one aspect comprising the steps of locating a stop device to restrict the first sensor to a known position outside the sensing movement range when the sensor is engaged with the stop device, selectively applying force to the first sensor to move it into contact with the stop device, measuring the force applied by the force generator and providing a measured force signal representative of the force applied by the force generator to move the first sensor into contact with the stop device, storing in a memory a reference force used to move the first sensor from a selected position at which the first sensor was subjected to a first force to the stop device, controlling the force generator to apply force to the first sensor to move it from an unknown position resulting from an unknown force acting upon the first sensor to the stop device, receiving the measured force signal from the force gauge, retrieving the reference force from the memory, and determining the value of the unknown force based on comparing the reference force to the measured force.

In a mounting system in accordance with the invention, there is provided a sensor mounting system for mounting a first sensor that moves within a range when sensing a physiological parameter and a second sensor that determines the position of the first sensor; the response of the sensor system being dependent upon the positioning; of the first and second sensors with respect to each other. The mounting system comprises a first housing within which the first sensor is mounted and a second housing within which a stop device is located so as to restrict the first sensor to a known position outside its sensing movement range when the sensor is engaged with the stop device. Wherein the first housing and second housing are movable in relation to each other along the direction of movement of the first sensor to provide for the sensing movement range of the first sensor and to locate the stop surface outside that movement range so that the first sensor is located at the particular position and further, wherein the second and first housings are movable in relation to the second sensor so that the first sensor may be located at the particular position in respect to the first sensor.

The novel features that are believed to be characteristic of the invention together with further objects and advantages thereof will be more readily understood from the following descriptions considered in connection with the accompanying drawings.

DETAILED DESCRIPTION OF THE PREFERRED EMBODIMENTS

Figure 1:
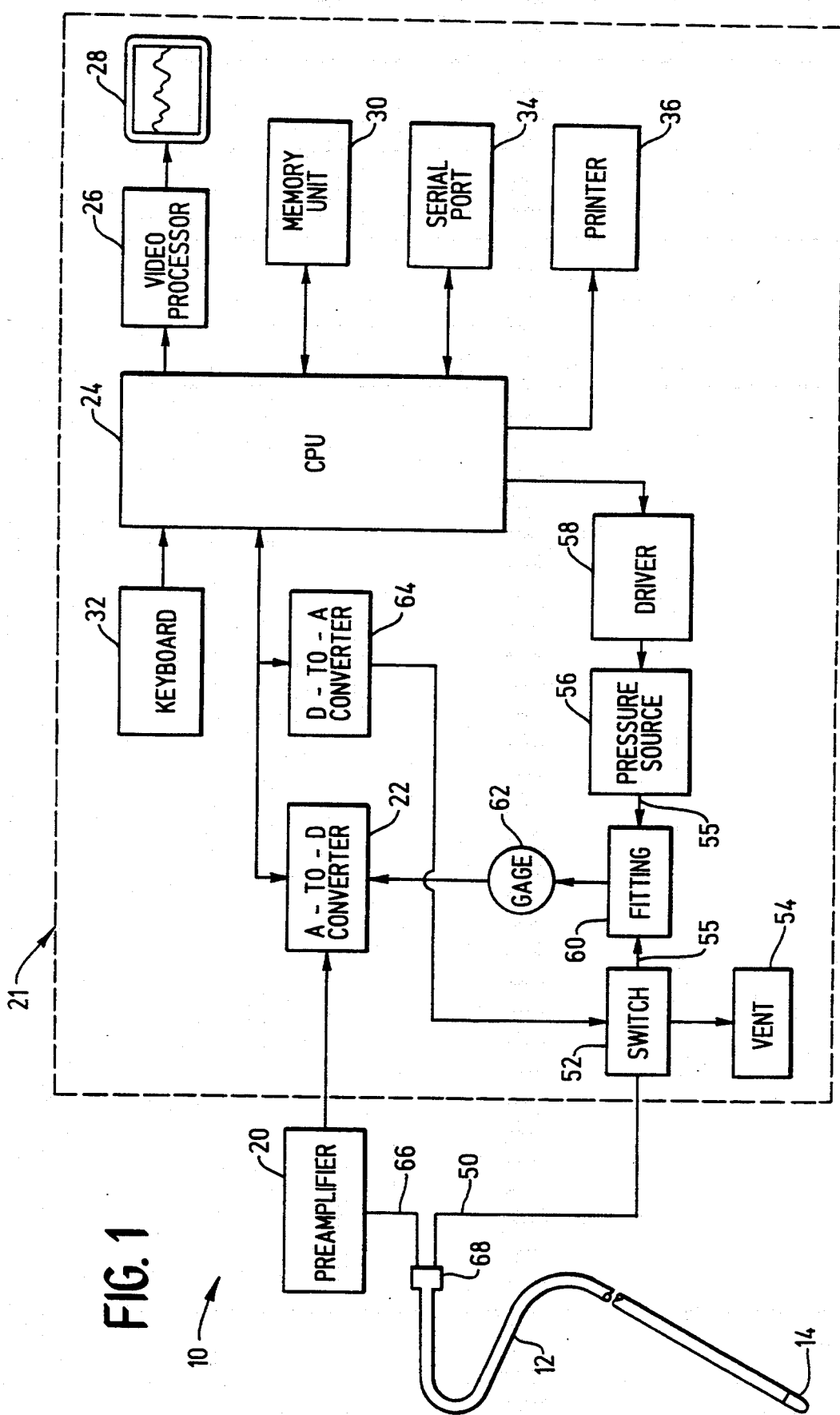
FIG. 1 is a block diagram of a transducer calibration system in accordance with the invention.

In the following description, like reference numerals are used to refer to like or corresponding elements in the different figures of the drawings. Referring now to the drawings with more particularity, in FIG. 1 there is shown a block diagram of a transducer calibration system 10 in accordance with the principles of the present invention. The system 10 is connected to a catheter 12 having a pressure transducer 14 mounted in its distal tip. In this case, the catheter 12 is usable for intracranial pressure monitoring applications and includes a transducer 14 having a bellows that moves in response to sensed intracranial pressure. Such a transducer configuration is shown in FIG. 2 where the distal tip opening 16 is oil-fried 17 for transmission of the pressure of intracranial fluids to the bellows 18. The bellows 18 moves longitudinally in the catheter 12 body in response to intracranial pressure experienced and an optical fiber system 42 monitors the bellows position and provides a position signal as will be described in more detail below.

Referring again to FIG. 1, the catheter 12 provides an output signal representative of the position of the bellows and a preamplifier 20 is placed in the line for amplifying the signal. Such a catheter with a fiber optic transducer system is available from Camino Laboratories, Inc., San Diego, Calif. and has a model no. of 110-4B. The coupling block 68 at the proximal end of the catheter may contain light-to-electrical and electrical-to-light transducers and other devices, as discussed below.

The output signal from the catheter 12 is provided via the preamplifier 20 to an instrument 21 having an analog-to-digital converter 22 that provides a corresponding digital signal to a central processing unit 24 ("CPU"). The CPU may take many forms; for example, a commercially available integrated circuit microprocessor having the INTEL model designation of 8086. The CPU 24 provides a video signal to a video processor 26 for display on a video monitor 28. Programs and data for the CPU 24 are stored in a memory unit 30, such as a magnetic or optical storage device, and communications with the CPU 24 may occur with a keypad or keyboard 32 and with a serial port 34. Data may also be output by the CPU 24 to a printer 36.

Referring now to FIG. 2, the catheter 12 includes a vent tube 38 for venting to atmospheric pressure the space 40 between the fiber optic transducer system 42 and the bellows end 44. The bellows end 44 may be formed with a highly reflective surface to reflect light from an emitter optical fiber 46 to a receiver optical fiber 48. Venting the space 40 permits movement of the bellows 18 without opposing forces that may be developed by air pressure if the space 40 were closed.

Returning now to FIG. 1, the vent tube 38 is connected at the proximal end of the catheter 12 to a fluid line 50. The fluid line 50 is used to control the pressure in the vent tube 38. A switch 52 is used to switch the fluid line 50 between an atmospheric pressure $P_{ATM}$ inlet 54 and pressure provided by a controllable pressure source 56. The controllable pressure source 56 is capable of applying pressures less than atmospheric. The controllable pressure source may take many forms; for example, a Pancake Cylinder made by Fabco-Air Inc. having a model no. of B-121-X. In another embodiment, a syringe may be used. The pressure source driver 58 controls the pressure source 56 to control the pressure applied to the vent tube 38 and may comprise a lead screw type arrangement or other motor driven system such as a Linear Actuator having a model no. of 36443-12 and stepper motor driver from Haydon Switch & Instrument, Inc.

Included in the fluid line 55 between the switch 54 and the pressure source 56 is a fitting 60 that permits a pressure gauge 62 to monitor the pressure in the fluid line 55. When the switch 52 is controlled to apply pressure from the controllable pressure source 56 directly to the fluid line 50, the gauge 62 then also measures the pressure in the fluid line 50. The sensed pressure from the pressure gauge 62 is provided to the A-to-D converter 22 to be converted to a digital signal and provided to the CPU 24. The CPU 24 also controls the switch 52 in the fluid line to switch between the vent 54 and the controllable pressure source 56 in accordance with an embodiment of the method of the invention, as is described in further detail below. A digital control signal from the CPU 24 is applied to a digital-to-analog ("D-to-A") converter 64 for conversion into an analog signal for control of the switch 52. In both the cases of the switch. 52 and the gauge 62, A-to-D and D-to-A converters are shown separately. However, other devices may be used in which the converters are incorporated into the device itself. For example, a pressure gauge may be used that outputs a digital signal rather than an analog signal.

Figure 2:
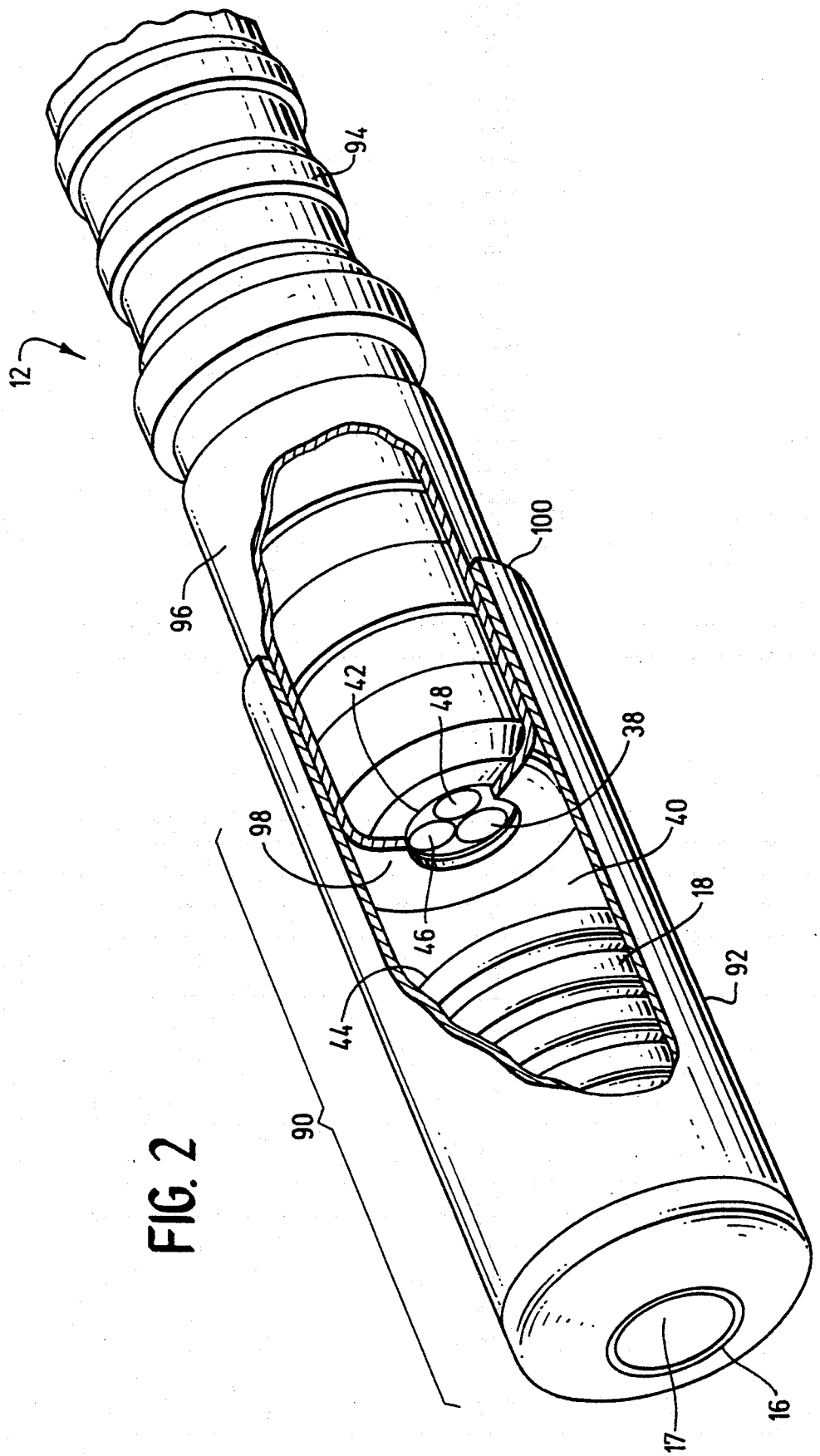
FIG. 2 is a partially cutaway perspective view of a pressure sensor with a part of a calibration system in accordance with the invention.
Figure 3:
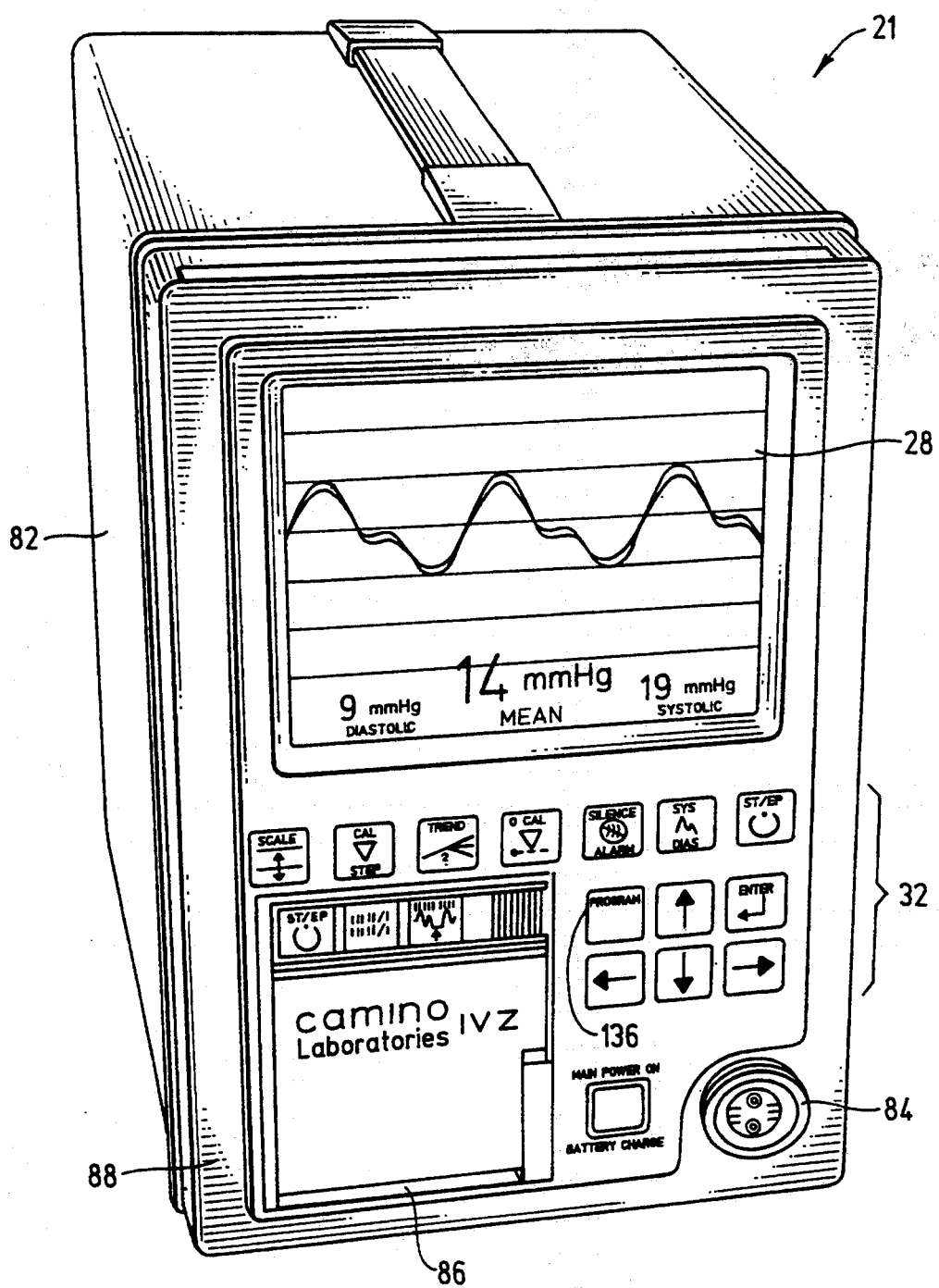
FIG. 3 is a perspective view of an instrument that includes various aspects of a transducer calibration system in accordance with the invention.

Thus, as shown in FIG. 1, the CPU 24 monitors the pressure in the fluid line 50 connected to the vent tube 38 of the catheter 12, controls the fluid line switch 52 to apply either atmospheric pressure $P_{ATM}$ or the pressure generated by the controllable pressure source 56 to the fluid line 50, controls the pressure applied to the fluid line 50 by the pressure source 56 through the driver 58, and monitors the position of the bellows 18 of the catheter 12 through the output electrical line 66 from the proximal end of the catheter that contains the pressure sense data from the optical fiber transducer system 42.

As discussed briefly above, the controllable pressure source 56 may be a syringe or other variable volume reservoir driven by a stepper motor as the driver unit 58. The reservoir 56 contains a fluid, such as air, and movement of the syringe plunger in the syringe barrel will cause movement of that fluid through the fluid line 55 connected to the nozzle of the syringe. A commercially available stepper motor and associated controller may be used provided that they are satisfactorily responsive to control signals to cause discrete changes in the pressure applied by the syringe at the resolution desired.

The fitting 60 may be a common "T" fitting and the pressure gauge 62 may be model 24PC-FA1D made by Honeywell MicroSwitch having an address of Freeport, Ill. The switch 52 may be a solenoid valve such as the one having a model no. of 401-37 and available from Humphrey Products Co. having an address of Kalamazoo, Mich. The vent device 54 may include a filter to prevent foreign particles from entering the fluid line 50 and vent tube 38 of the catheter 12.

The A-to-D and D-to-A converters, CPU, keypad, gauge, switch, fitting, pressure source and driver, vent, memory, serial port, video card and video display may all be located in a single instrument 21 such as that shown in FIG. 1. The instrument 21 includes a housing 82 having a catheter port 84 for coupling to a catheter 12 through the preamplifier 20. The serial port is not shown in the figure and is located at the back, as is the printer port. In another embodiment, the housing 82 may also contain a reduced-size printer, the printed output of which may be provided to the operator through a slot 86 on the front panel 88.

Referring again to FIG. 2, a partially cut-away perspective view of the distal end of the pressure monitoring catheter 12 is shown. In the distal end is mounted a pressure sensor 90 that, in this case, comprises a movable sensing element that is shown as the bellows 18 mounted in an outer housing 92. The pressure of the intracranial or other fluid to be sensed is transmitted to the bellows 18 through the oil 17 located in the inlet port 16. This pressure will cause the bellows 18 to move in accordance with that pressure. The bellows 18 includes a reflective surface 44 that is efficient in reflecting incident light. Facing the bellows 18 is the main shaft 94 of the catheter 12 that includes the two optical fibers 46 and 48 and the vent tube 38. Also included in the pressure sensor 90 is an inner housing 96 having a stop surface 98. The inner housing 96 is attached to the outer housing 92 at the proximal end 100 of the outer housing in one embodiment by epoxy or welding. As is described in more detail below, both the inner 96 and outer 92 housings can be independently moved in relation to the main catheter body 94. After they have been located as desired, the outer housing 92 can be welded to the inner housing 96 and the inner housing 96 can be welded to the main catheter body. Thus, two controls over the locations of parts of the transducer systems are provided. As will be described in more detail below, this arrangement greatly facilitates manufacturing the transducer systems and the transducer calibration system and enables increased accuracy in operation of the catheter and the transducer calibration system.

Figure 6:
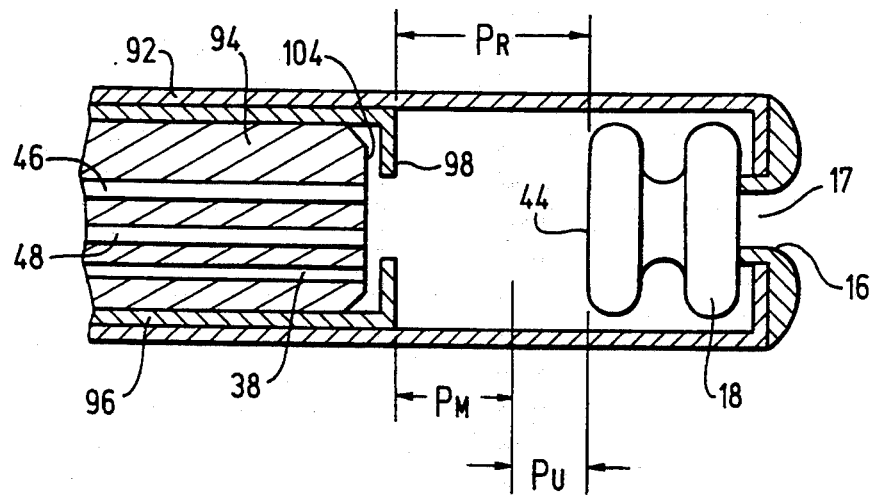
FIG. 6 presents a diagram showing the movement range of the sensor including both normal operation movement and calibration movement.

Referring now to FIG. 6, a cross-sectional side view of the catheter 12 is shown in which the sensing element or bellows 18 is responsive to internal pressure $P_{int}$ applied through the vent tube 38 and to external pressure $P_{ext}$, such as intracranial pressure, applied through the oil 17 disposed in the bellows opening 16. The bellows is mounted such that its sensing range does not include contact with the stop surface. In the embodiment shown, the stop surface is proximal to the bellows.

The reflective surface 44 faces the two optical fibers 46 and 48 to reflect light provided by the emitter fiber 46 back to the receiver fiber 48 in a manner well known to those skilled in the art. By processing the reflected light, the position of the reflective surface 44 can be determined and thus, the pressure sensed by the transducer 90. The vent tube or lumen 38 couples the controlled pressure fluid from the controllable pressure source 56 or air at atmospheric pressure to the inside part of the housing 92 as selected by the switch 52 shown in FIG. 1.

Figure 5:
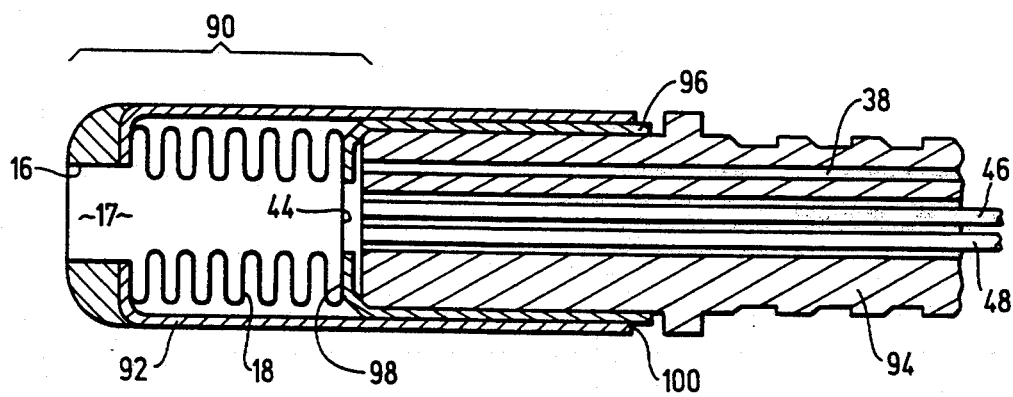
FIG. 5 illustrates a cutaway view of the distal end of the catheter and calibration system of FIG. 2 showing the pressure sensing element at the stop surface that comprises the calibration position.

Referring now to FIG. 5, the bellows 18 has been moved to a second position which in this case, is the calibration position against the stop surface 98 provided by the inner housing 96. This stop surface 98 is a physical stop that provides a known and repeatable position for the reflective surface 44. This stop surface 98 is also located outside the sensing range of movement of the bellows 18 under normal operational pressures. Therefore, additional force is required to move the bellows 18 to the calibration position where the reflective surface 44 abuts the stop surface 98. Force in the form of a pressure on the proximal side $P_{int}$ of the bellows lower than the pressure on the distal side $P_{ext}$ must be applied. To return the bellows to a point within its normal range of movement, the pressure $P_{int}$ must be relieved. Thus, by controlling the pressure applied to the vent lumen 38, the reflective surface 44 of the bellows 18 can be moved to a known position; i.e., the stop surface 98, for use in conducting a calibration operation.

The use of the stop surface 98 at a known point outside the normal range of movement of the bellows 18 results in a highly accurate point of reference. By previously measuring the amount of pressure reduction required to move the bellows 18 from its position at atmospheric pressure to the calibration position and storing that amount of pressure reduction in a memory, it may be referred to while the sensor is in vivo for use in a calibration operation. Then when in vivo calibration is desired, the amount of pressure reduction required to move the bellows from its present unknown position to the calibration position is determined and this pressure is compared to the stored pressure as follows:

$$P_M + P_U = P_R \qquad \text{eq.(1)}$$

where:

$P_M$ = the change in pressure necessary to move the bellows from the unknown position to the stop position (measured pressure)

$P_U$ = the pressure acting on the bellows (patient pressure) that moves it from the equilibrium position to the unknown position (unknown pressure)

$P_R$ = the change in pressure necessary to move the bellows from the equilibrium position to the stop position By rearranging equation 1, the calculation needed to derive the unknown pressure is more apparent:

$$P_U = P_R - P_M \qquad \text{eq.(2)}$$

Thus by storing the reference pressure $P_R$ determined in vitro, and then measuring the pressure $P_M$ needed to move the sensor to the stop position, the unknown pressure $P_U$ can be determined. In the embodiment shown in FIG. 1, the reference pressure $P_R$ would be stored in the memory 30 by the processor 24 and retrieved when performing a calibration procedure. It may also be stored in a memory device, such as an EEPROM, accompanying the catheter so that the catheter can be connected to another instrument while in use. Such a memory device may be located in the termination block 68 at the proximal end of the catheter (FIG. 1). The $P_R$ may be determined just before use of the sensor on a patient. The processor would then use it and the measured pressure $P_M$ to calculate the unknown pressure $P_U$ as shown in equation (2). The calculated unknown pressure $P_U$ would then be used to correct any zero shift that resulted in error in the displayed pressure.

Figure 4:
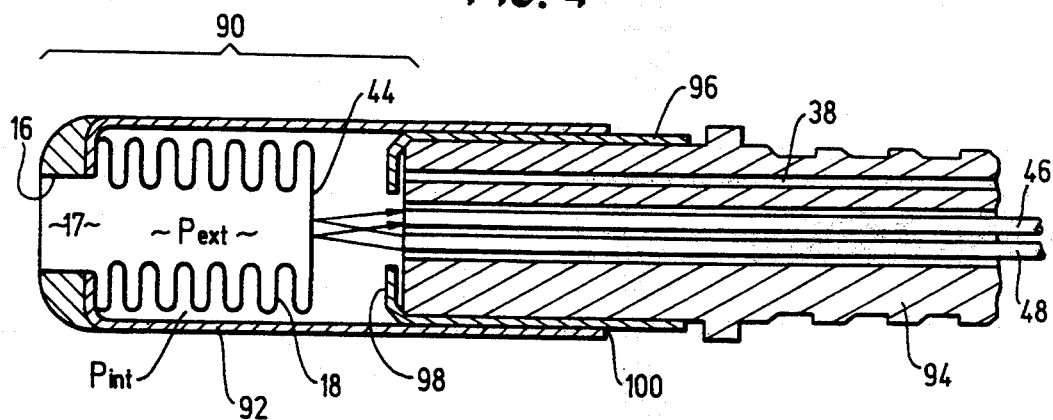
FIG. 4 illustrates a cutaway view of the distal end of the catheter and calibration system of FIG. 2 showing the pressure sensing element at a position in the normal range of movement.

From a review of FIGS. 4 and 5, it will be noted that two sensors are involved. The first sensor is the bellows or pressure sensing element. The second sensor is the light system established by the two optical fibers 46 and 48. As described above, the pressure sensing element must be positioned properly so that there exists a sensing movement range and a stop or reference position beyond the sensing range. In this case, the reference position is at a point beyond the position the sensor would be in if it experienced the maximum expected sensing pressure. However, the light system also has inherent response characteristics that must be taken into account when manufacturing the system shown in these figures.

Because one sensor, whether it be ate pressure sensing device or the light sensing system, rarely has the same response characteristics as another sensor, each sensor needs to be calibrated during manufacture. The arrangement of inner and outer housings in accordance with the invention satisfies a long standing need to do so efficiently, accurately, and at decreased expense.

Figure 7:
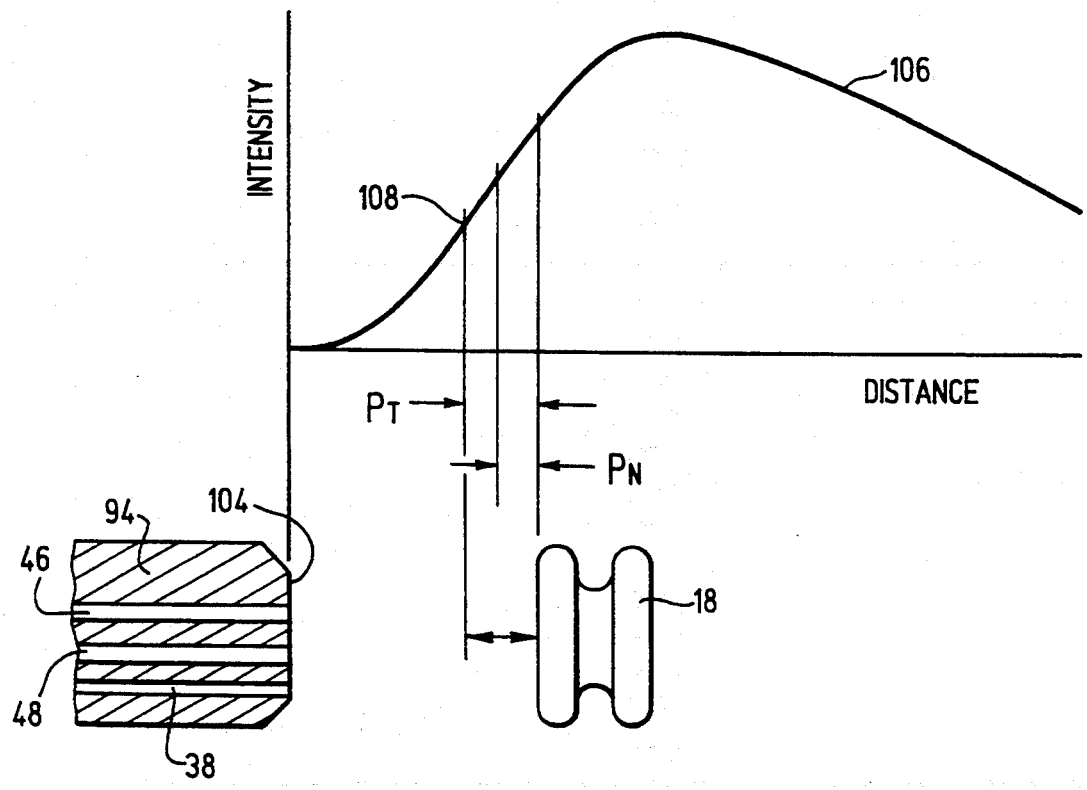
FIG. 7 presents a graph of the operation of the light transducer showing the light intensity versus distance from the sensor.

In the system shown, one optical fiber 46 emits light to be reflected by the reflective surface 44 of the bellows. The other optical fiber 48 receives that reflected light. Characteristics of the received light may be used to determine the position of the pressure sensor 18 and the pressure sensed. Referring now to FIG. 7, a sample response graph 106 of a light sensing system is shown. To more clearly explain rite points to be made by the graph, a drawing of the distal ends 104 of the optical fibers has been positioned at the zero distance point on the horizontal axis. A bellows 18 has been drawn below that same axis and its range of movement indicated by lines intersecting the plotted intensity 106 graph line. The lines labeled $P_N$ indicate the normal or sensing range of movement of the bellows. That is, the range of movement in response to the specified range of pressures that may be sensed with that sensor. In the case shown, the bellows 18 has been positioned so that the normal range of movement $P_N$ occurs in a high slope portion of the response curve 106 of the light sensor 42. The total range of movement of the bellows including its position at the stop surface is indicated by $P_T$. As is also apparent, the position 108 at the stop surface also falls in a high slope portion of the graph 106. Therefore, the bellows 18 must be located away from the optical fiber ends 104 by a certain distance to be in the high slope range of operation of the light sensor 42. This distance varies from light sensor to light sensor.

Thus, two sensors having independent response characteristics need to be calibrated during manufacture. It is desirable to provide a system for calibrating each sensor independently so that interaction between the two during calibration is minimized. That is, it is desirable that the calibration of one either not at all or only minimally depend on the calibration of the other.

In the case of the first sensor, or bellows in this embodiment, the bellows must have a full range of movement when subjected to the specified sensing pressures in the applications to which it will be applied. Additionally, it must have a stop or reference position beyond that specified sensing pressure range. The stop surface must be located at a particular position to accomplish the latter goal. However, that entire range of movement of the bellows, including the stop surface position, must fall, in this embodiment, within a linear response range for this particular optical system 42. Achieving these two calibration objectives is accomplished in the arrangement in accordance with the invention by moving the inner housing into the outer housing until the inner housing contacts the bellows. The bellows is then subjected to a pressure greater than the highest expected pressure but within the range of pressure that can be generated by the controllable pressure source. Because the inner housing started out in contact with the bellows before the pressure was applied, the bellows has moved the inner housing in relation to the outer housing during application of the pressure and the bellows is still in contact with the stop surface 98. The housings can now be bonded together by an adhesive such as epoxy or by welding or other means.

Then the second sensor; i.e., the light transducer, may be calibrated during manufacture by moving the bonded outer/inner housing combination along the shaft 94 of the catheter until the optimum optical response is realized when the bellows is moved throughout its total range of movement. The inner housing 96 can then be bonded to the catheter shaft 94 by use of an adhesive or by welding. As can be appreciated, the arrangement provided by the invention results in an ability to quickly and accurately calibrate the transducer during manufacture regardless of the performance differences between individual pressure sensors and optical sensors. Where in most cases the small size of the components would cause severe difficulties during the manufacturing process, the arrangement of the system in accordance with the invention results in relative ease and allows for increased accuracy during manufacture.

Figure 8:
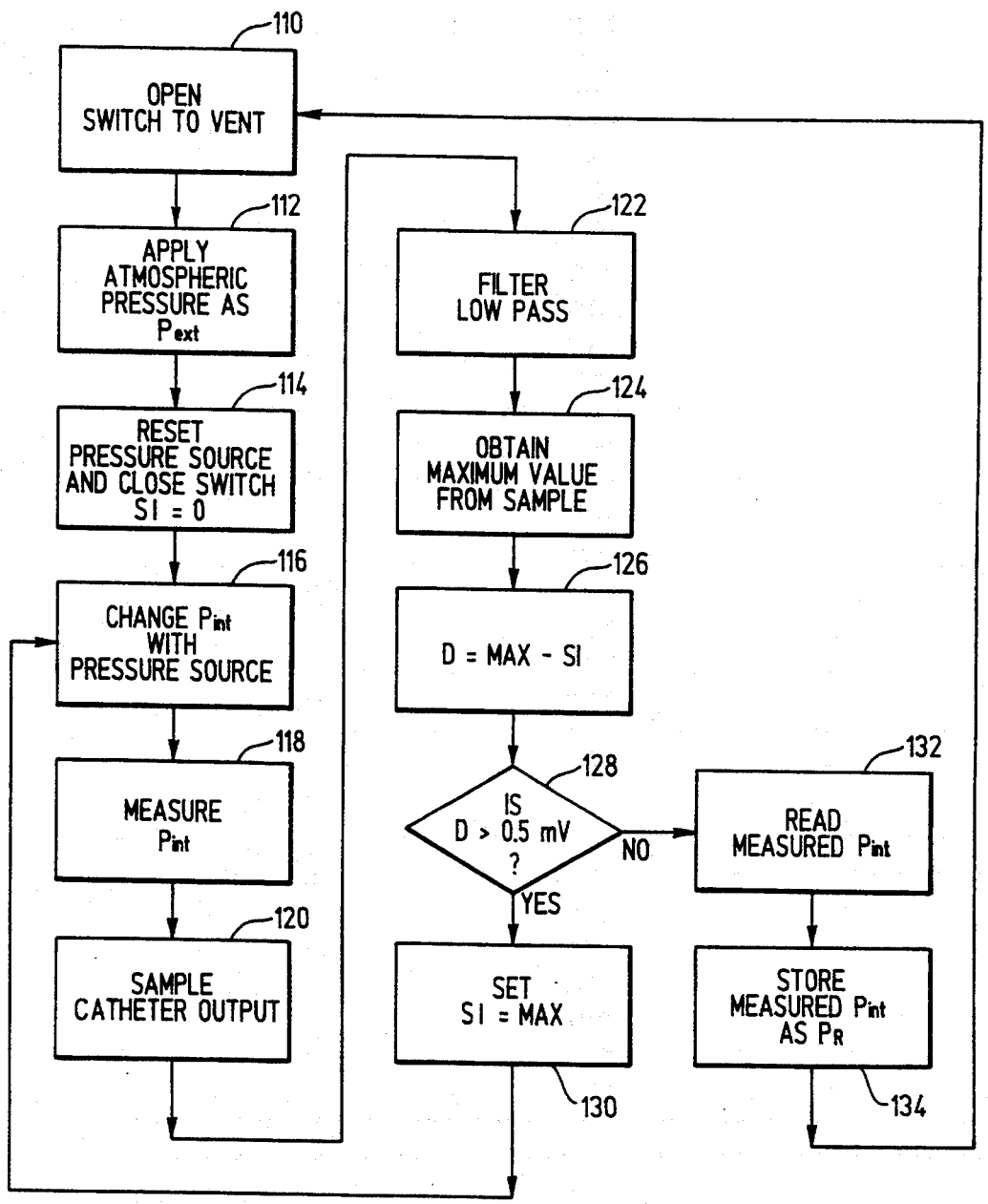
FIG. 8 is a flow chart illustrating an in vitro calibration method in accordance with the principles of the invention.

Referring now to both FIGS. 8 and 1, an embodiment of an aspect of the method of the invention is presented in the form of a flow chart. In the procedure shown, the transducer 90 is initially calibrated, such as during manufacture or immediately before use on a patient. The switch 52 is opened 110 to vent the vent tube 38 to atmospheric pressure $P_{ATM}$. A known pressure such as atmospheric pressure $P_{ATM}$ is also applied to the bellows as an external pressure $P_{ext}$ 112. The pressure source 56 is then reset 114, such as by moving it to its minimum stroke position and the switch is closed so that only pressure from the pressure source 20 is coupled to the proximal side of the bellows 18 as an internal pressure $P_{int}$. At the same time, the data value SI in the CPU 24 is set to zero. Next the pressure source 56 decreases 116 the pressure in the vent tube 38 by an incremental amount while the $P_{int}$ is measured 118 by the gauge 62. The catheter output is sampled 120 and is low pass filtered 122. The maximum pressure indicated by the catheter sample is obtained 124 from this incremental pressure change and is compared 126 to the last pressure value SI. If the difference D exceeds 128 a predetermined threshold value, such as 0.5 mV, the data value SI is reset 130 to that maximum pressure measured and the process of incrementally varying the pressure is repeated.

In the case where the maximum pressure value D 128 does not change by the predetermined amount, the processor concludes that the reflective surface 44 is against the stop surface 98 and reads 132 the pressure gauge 62 to determine tire reference pressure $P_R$. This measured $P_R$ is stored 134 in a memory 30 for later reference. The catheter may now be used.

During each discrete pressure variance cycle described above, the CPU 24 signals the pressure source 56 to cause incremental decreases in the pressure on the bellows 18. This change in pressure causes the bellows 18 to move in a direction towards the stop surface 98. When the pressure indicated by the optical fiber system ceases to change, the processor then stops this in vitro calibration and stores the amount of pressure $P_R$ required to move the bellows from the position caused by the known external pressure $P_{ATM}$ to the reference position at the stop surface. In the preferred embodiment, the increments in pressure are approximately 2 mm Hg.

In the preferred embodiment, approximately one thousand samples are obtained during a three second period to obtain the maximum transducer value. A digital low pass filter function is provided by the CPU 24 that is used to eliminate noise in the sample data. Digital filtering is well known to those skilled in the an and no further details are given here.

Figure 9:
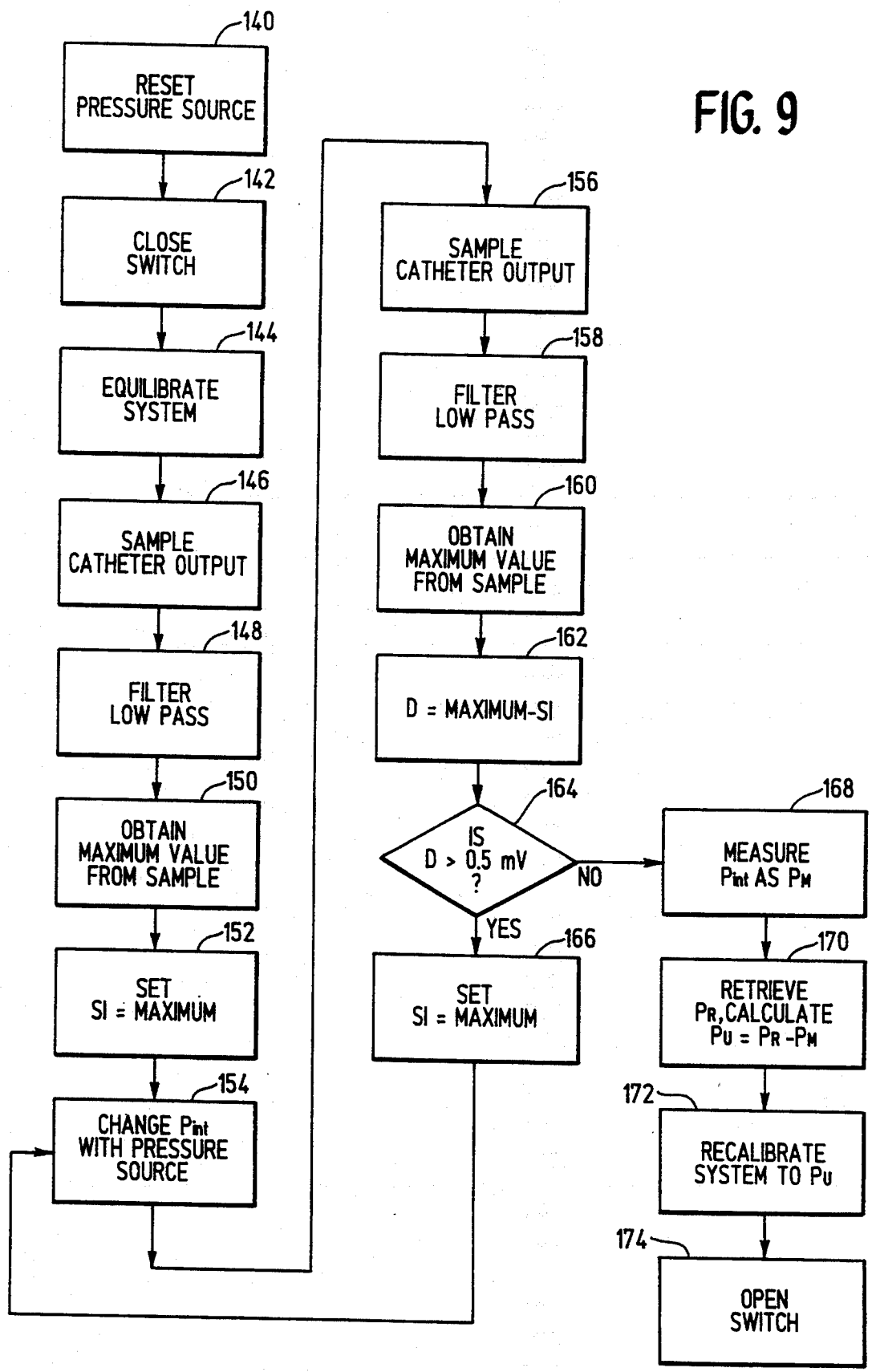
FIG. 9 is a flow chart illustrating an in vivo calibration method in accordance with the principles of the invention.

Referring now to FIGS. 9 and 1, an embodiment of a process of in vivo calibration of the transducer in accordance with an aspect of the invention is presented. When recalibration of the system is desired without removal of the catheter from the patient, the CPU 24 receives a signal from a user to perform an in vivo calibration routine, such as by the user pressing a button on the front panel 88 of the instrument 21, such as the "PROGRAM" button 136 (FIG. 5). The CPU 24 then resets 140 the controllable pressure source 56 and closes 142 the switch 52 so that only pressure supplied by the pressure source 56 provides $P_{int}$ (the switch 52 was open to atmospheric pressure $P_{ATM}$ for operation). The system is equilibrated for some selected time period such as one second 144 to allow the vent tube 38 pressure to equalize. The CPU 24 samples signals from the catheter 146 for a time necessary to receive a maximum transducer value. In the preferred embodiment, one thousand samples are obtained during a three second period to obtain the maximum transducer value. The CPU 24 performs a digital low pass filtering function 148 that is used to eliminate noise in the sample data. The maximum transducer monitor value is obtained 150 from the sample data and is assigned the data value SI 152.

Next, the CPU 24 controls a series of discrete pressure variance cycles to determine the exact amount of pressure $P_{int}$ necessary to cause the bellows 18 to contact the stop surface 98. During each discrete pressure variance cycle, the CPU 24 first signals the pressure source 56 to cause incremental decreases 154 in pressure on the proximal side of the bellows. This change in pressure causes the bellows to move in a proximal direction towards the stop surface 98. During these incremental adjustments in the pressure, signals from the catheter are sampled 156 and digitally low-pass filtered 158 to eliminate noise in the sample data, and the maximum pressure value is obtained from each sample 160. In the preferred embodiment, one thousand data samples are obtained during a three second period to obtain the maximum transducer value.

During in vivo calibration, the heart beat causes continuous, pulsate changes in the sensed pressure. As the systolic (maximum) component is highest in magnitude, it will be affected first by the stop. The maximum transducer monitor value must be measured at a time when the detector is at the maximum systolic pressure position, otherwise the bellows 18 may be positioned too close to the stop surface 98 and clipping of the systolic maximum pressure waveform will occur. Clipping will cause the bellows to move randomly thereby making sampling of a maximum transducer monitor value difficult. The CPU 24 receives the pressure waveform from the catheter, tracks the systolic pressure and determines the peak 160.

The maximum value obtained 160 is then compared to the SI value 162 and if the difference D exceeds a predetermined value 164, such as 0.5 mV, the SI data value is changed to the MAX value 166. The process of incrementally moving the pressure source 56 is repeated.

The above-described discrete pressure variance cycle is repeated until the transducer differential D is less than or equal to the predetermined value (0.5 mV). Upon this occurrence, the bellows 18 is considered to have made contact with the stop surface 98. The CPU 24 then measures 168 the pressure $P_M$ through the gauge 62 required to move the bellows to the stop position from the unknown position. The processor retrieves the reference pressure $P_R$ and calculates the unknown pressure $P_U$ based on the measured pressure and reference pressure in accordance with eq. (2) above. The calculated pressure is then displayed and the system is now recalibrated. The switch 52 is then opened for further operation by the catheter.

The entire in vivo calibration process described above is automated and controlled by the CPU 24 after request by the operator. The process permits rapid recalibration of the sensing system without the need to remove the sensing system from the patient. Because of the unique construction and method of the calibration system in accordance with the principles of the invention, accuracy and speed in recalibrating result.

While particular forms of the invention have been illustrated and described, it will be apparent that various modifications can be made without departing from the spirit and scope of the invention.

I claim:

1. A calibration system for calibrating a sensor system having a first sensor that moves within a range when sensing a physiological parameter, the sensor system also having a processing system that monitors the position of the first sensor and provides an output signal representative of the physiological parameter based on the monitored position of the first sensor, the calibration system comprising:
   a stop device located so as to restrict the first sensor to a known position outside the sensing movement range when the sensor is engaged with the stop device;
   a controllable force generator that selectively applies force to the first sensor to move it into contact with the stop device;
   a force gauge that measures the force applied by the force generator and provides a measured force signal representative of the force applied by the force generator to move the first sensor into contact with the stop device; and
   a memory having stored therein a reference force used to move the first sensor from a selected position at which the first sensor was subjected to a first force to the stop device;
   wherein the processing system controls the force generator to apply force to the first sensor to move it from an unknown position resulting from an unknown force acting upon the first sensor to the stop device, receives the measured force signal from the force gauge, retrieves the reference force, and determines the value of the unknown force based on comparing the reference force to the measured force.

2. The calibration system of claim 1 wherein:
   the first sensor movement range comprises a maximum position at which the first sensor would be located should the physiological parameter reach a maximum predetermined level; and
   the stop device is located outside the first sensor movement range and beyond the maximum position.

3. The calibration system of claim 2 wherein the force generator selectively applies a reduced pressure against the first sensor to urge it into contact with the stop device.

4. The calibration system of claim 3 wherein:
   the first sensor is located in an enclosed area that surrounds one end of the first sensor;
   a vent tube is coupled to the enclosed area; and
   the reduced pressure is applied to the first sensor through the vent tube.

5. The calibration system of claim 2 wherein:
   the first sensor is mounted in an outer housing, the outer housing having a first opening for transferring the physiological parameter to the first sensor, the outer housing having a second opening;

an inner housing is mounted in the second opening of the first housing at a selected position and provides the stop device and an access port through which the force is applied by the force generator to the first sensor;

wherein the inner housing and associated stop device are mounted opposite the first opening and beyond the maximum position.

6. The calibration system of claim 1 wherein the processing system additionally controls the force generator to incrementally apply force to move the first sensing element into contact with the stop device.

7. The calibration system of claim 1 further for calibrating a sensor system that additionally comprises a second sensor that determines the position of the first sensor in sensing the physiological parameter, the second sensor being responsive to the distance of the first sensor from the second sensor, the calibration system further comprising:

a first housing within which the first sensor is mounted; and a second housing having the stop device;

wherein the first housing and second housing are movable in relation to each other along the direction of movement of the first sensor and are bonded to each other in a position to permit the sensing movement range of the first sensor and to locate the stop surface outside that movement range;

wherein the second housing is movable in relation to the second sensor so that the first sensor is locatable at a desired distance from the second sensor.

8. A method of calibrating a sensor system having a first sensor that moves within a range when sensing a physiological parameter, the sensor system also having a processing system that monitors the position of the first sensor and provides an output signal representative of the physiological parameter based on the monitored position of the first sensor, the method of calibrating comprising the steps of:

locating a stop device to restrict the first sensor to a known position outside the sensing movement range when the sensor is engaged with the stop device;

selectively applying force to the first sensor to move it into contact with the stop device;

measuring the force applied by the force generator and providing a measured force signal representative of the force applied by the force generator to move the first sensor into contact with the stop device;

storing in a memory a reference force used to move the first sensor from a selected position at which the first sensor was subjected to a first force to the stop device;

controlling the force generator to apply force to the first sensor to move it from an unknown position resulting from an unknown force acting upon the first sensor to the stop device;

retrieving the reference force from the memory; and determining the value of the unknown force based on comparing the reference force to the measured force.

9. The calibration method of claim 8 wherein the first sensor movement range comprises a maximum position at which the first sensor would be located should the physiological parameter reach a maximum predetermined level and the step of locating the stop device comprises locating the stop device outside the first sensor movement range and beyond the maximum position.

10. The calibration method of claim 9 wherein the method is further for calibrating a sensor system that additionally comprises a second sensor that determines the position of the first sensor in sensing the physiological parameter, the second sensor being responsive to the distance of the first sensor from the second sensor, the calibration method further comprising the steps of:

locating the first sensor in a first housing;

locating the stop device in a second housing;

moving the first housing and second housing in relation to each other along the direction of movement of the first sensor to locate the stop surface outside that movement range and bonding the first and second housings to each other once that position has been obtained; and moving the second housing in relation to the second sensor so that the first sensor is locatable at a desired distance from the second sensor.

11. The calibration method of claim 8 wherein the step of selectively applying force to the first sensor to move it into contact with the stop device comprises applying a reduced pressure against the first sensor to urge it into contact with the stop device.

12. The calibration method of claim 11 wherein the step of applying a reduced pressure comprises applying the pressure to the first sensor through a vent tube coupled to an enclosed area surrounding one end of the first sensor.

13. The calibration method of claim 8 wherein the step of selectively applying force to the first sensor to move it into contact with the stop device comprises the step of incrementally applying the force to move the first sensing element into contact with the stop device.

14. A calibration system for calibrating a sensor system having a first sensor that moves within a range when sensing a physiological pressure and a second sensor that determines the position of the first sensor, the second sensor providing a position signal representative of the position of the first sensor, the sensor system also having a processing system that monitors the position signal and provides an output signal representative of the physiological pressure based on the monitored position of the first sensor, wherein the first sensor movement range comprises a maximum position at which the first sensor would be located should the physiological parameter reach a maximum predetermined level, the calibration system comprising:

a stop device located so as to restrict the first sensor to a known position outside the sensing movement range when the sensor is engaged with the stop device, the stop device being located beyond the maximum position of the first sensor;

a controllable pressure generator that selectively applies pressure to the first sensor to move it into contact with the stop device;

a pressure gauge that measures the pressure applied by the pressure generator and provides a measured pressure signal representative of the pressure applied by the pressure generator to move the first sensor into contact with the stop device; and a memory having stored therein a reference pressure used to move the first sensor from a selected position at which the first sensor was subjected to a first pressure to the stop device;

wherein the processing system controls the pressure generator to apply pressure to the first sensor to move it from an unknown position resulting from an unknown pressure acting upon the first sensor to the stop device, receives the measured pressure signal from the pressure gauge, retrieves the reference pressure, and determines the value of the unknown pressure based on comparing the reference pressure to the measured pressure.

15. The calibration system of claim 14 wherein the pressure generator selectively applies a reduced pressure against the first sensor to urge it into contact with the stop device.

16. The calibration system of claim 15 wherein:
the first sensor is located in an enclosed area that surrounds one end of the first sensor;
a vent tube is coupled to the enclosed area; and
the reduced pressure is applied to the first sensor through the vent tube.

17. The calibration system of claim 14 wherein:
the first sensor is mounted in an outer housing, the outer housing having a first opening for transferring the physiological pressure to the first sensor, the outer housing having a second opening;
an inner housing is mounted in the second opening of the first housing at a selected position and provides the stop device and an access port through which the pressure is applied by the pressure generator to the first sensor;
wherein the inner housing and associated stop device are mounted opposite the first opening and beyond the maximum position.

18. The calibration system of claim 14 wherein the processing system additionally controls the pressure generator m incrementally apply pressure to move the first sensing element into contact with the stop device.

19. The calibration system of claim 18 further comprising:
a first housing within which the first sensor is mounted; and
a second housing having the stop device;
wherein the first housing and second housing are movable in relation to each other along the direction of movement of the first sensor and are bonded to each other in a position to permit the sensing movement range of the first sensor and to locate the stop surface outside that movement range;
wherein the second housing is movable in relation to the second sensor so that the first sensor may be located at a desired distance from the second sensor.

20. A sensor mounting system for mounting a first sensor that moves within a range when sensing a physiological parameter and a second sensor that determines the position of the first sensor, the responses of both the first and second sensors being dependent upon their positioning at a particular location in respect to the parameter to be sensed, the mounting system comprising:
a first housing within which the first sensor is mounted;
a second housing within which a stop device located so as to restrict the first sensor to a known position outside its sensing movement range when the sensor is engaged with the stop device is mounted;
wherein the first housing and second housing are movable in relation to each other along the direction of movement of the first sensor to provide for the sensing movement range of the first sensor and to locate the stop surface outside that movement range so that the first sensor is located at the particular position;
wherein the second and first housings are movable in relation to the second sensor so that the first sensor is locatable at the particular position in respect to the first sensor.

21. The sensor mounting system of claim 20 wherein the first sensor comprises a movable device, the position of which depends upon the physiological parameter sensed;
the second sensor comprises an optical location system that uses light energy to locate the position of the first sensor;
wherein the first and second housing are adapted to be located in respect to each other to provide for the movement range of the first sensor and are further adapted to then be located in respect to the second sensor to locate the second sensor at the particular position frown the first sensor.

22. A method of mounting a plurality of sensors of a sensor system in relation to each other, the plurality comprising a first sensor that moves within a range when sensing a physiological parameter and a second sensor that determines the position of the first sensor, the responses of both the first and second sensors being dependent upon their positioning at a particular location in respect to the parameter to be sensed, the method comprising the steps of:
mounting the first sensor in a first housing;
mounting in a second housing a stop device located so as to restrict the first sensor to a known position outside its sensing movement range when the sensor is engaged with the stop device;
moving the first housing and second housing in relation to each other along the direction of movement of the first sensor to provide for the sensing movement range of the first sensor and locating the stop surface outside that movement range so that the first sensor is located at the particular position; and
moving the second and first housings in relation to the second sensor so that the first sensor is locatable at the particular position in respect to the first sensor.

* * * * *